US012673204B2

(12) United States Patent
Min et al.

(10) Patent No.: US 12,673,204 B2
(45) Date of Patent: Jul. 7, 2026

(54) COCHLEAR IMPLANT SYSTEM USING COMPATIBLE EXTERNAL DEVICE

(71) Applicant: TODOC Co., Ltd., Seoul (KR)

(72) Inventors: Kyou Sik Min, Suwon-si (KR); Ho Seung Lee, Seoul (KR); Jeong U Lim, Osan-si (KR); Eun Su Kim, Seoul (KR)

(73) Assignee: TODOC Co., Ltd., Seoul (KR)

( * ) Notice: Subject to any disclaimer, the term of this patent is extended or adjusted under 35 U.S.C. 154(b) by 265 days.

(21) Appl. No.: 18/286,498

(22) PCT Filed: May 2, 2022

(86) PCT No.: PCT/KR2022/006266
§ 371 (c)(1),
(2) Date: Oct. 11, 2023

(87) PCT Pub. No.: WO2022/235038
PCT Pub. Date: Nov. 10, 2022

(65) Prior Publication Data
US 2024/0189595 A1 Jun. 13, 2024

(30) Foreign Application Priority Data
May 3, 2021 (KR) ........................ 10-2021-0057331

(51) Int. Cl.
*A61N 1/36* (2006.01)
*A61N 1/05* (2006.01)
*A61N 1/372* (2006.01)
(52) U.S. Cl.
CPC ....... *A61N 1/36038* (2017.08); *A61N 1/0541* (2013.01); *A61N 1/37235* (2013.01); *A61N 1/37252* (2013.01)

(58) Field of Classification Search
CPC .............. A61N 1/36038; A61N 1/0541; A61N 1/37235; A61N 1/37252; A61N 1/36142;
(Continued)

(56) References Cited

U.S. PATENT DOCUMENTS 7,502,653 B2 3/2009 Daly
8,784,312 B2 7/2014 van Dijk et al.
(Continued)

FOREIGN PATENT DOCUMENTS

KR 10-0977525 B1 8/2010
KR 10-2010-0122001 A 11/2010
(Continued)

OTHER PUBLICATIONS

Request for the Submission of an Opinion for Korean Application No. 10-2021-0057331 mailed on Sep. 28, 2022, with its English translation, 7 pages.
(Continued)

*Primary Examiner* — Brian T Gedeon
(74) *Attorney, Agent, or Firm* — Mandar A. Joshi; Bret E. Field; Bozicevic, Field & Francis LLP

(57) ABSTRACT

A cochlear implant system using a compatible external device includes an external device that keeps mapping data, which are obtained by measuring a biological response to an electrical stimulation signal of an internal device implanted in a cochlear conduct of a user, for each internal device, determines whether there is compatibility with a target internal device, and converts sound into an electrical signal in accordance with mapping data of the target internal device of a plurality of pieces of mapping data, and a target internal device that receives an electrical signal from the external device, converts the electrical signal into an electrical stimu-
(Continued)

lation signal, and stimulates the auditory nerve of a cochlea with the electrical stimulation signal when the external device is compatible.

2 Claims, 4 Drawing Sheets

(58) Field of Classification Search
CPC . A61N 1/36135; A61N 1/36146; G16H 40/63
See application file for complete search history.

(56)                      References Cited

U.S. PATENT DOCUMENTS

| | | | |
|---|---|---|---|
| 2010/0016922 A1* | 1/2010 | Daly | A61N 1/37252 |
| | | | 607/57 |
| 2014/0309712 A1 | 10/2014 | Masaki et al. | |
| 2014/0350641 A1 | 11/2014 | Faltys et al. | |
| 2020/0269057 A1 | 8/2020 | Mazanec et al. | |
| 2020/0305000 A1 | 9/2020 | Obaidi | |

FOREIGN PATENT DOCUMENTS

| | | | |
|---|---|---|---|
| KR | 10-2016-0132941 A | 11/2016 | |
| KR | 10-2019-0043943 A | 4/2019 | |
| KR | 10-2013964 B1 | 8/2019 | |
| KR | 10-2021-0044596 A | 4/2021 | |
| WO | WO2007090243 A1 | 8/2007 | |
| WO | WO2017100866 A1 | 6/2017 | |
| WO | WO2017151106 A1 | 9/2017 | |
| WO | WO2019186373 A1 | 10/2019 | |
| WO | WO2020139375 A1 | 7/2020 | |

OTHER PUBLICATIONS

Written Decision of Registration for Korean Application No. 10-2021-0057331 mailed on Feb. 27, 2023, with its English translation, 2 pages.

International Search Report for PCT Application No. PCT/KR2022/006266 mailed Aug. 10, 2022, with its English translation, 5 pages.

Examination Report issued by the Australian Patent Office concerning the corresponding AU patent application No. 2022271094, dated Sep. 30, 2024, 8 pages.

Notice of Acceptance for Patent Application issued by the Australian Patent Office concerning the corresponding AU patent application No. 2022271094, dated Sep. 3, 2025, 3 pages.

Extended European Search Report issued by the European Patent Office (EPO) concerning the corresponding EP patent application No. 22799081.9, dated Feb. 11, 2025, 8 pages.

* cited by examiner

<u>100</u>

COCHLEAR IMPLANT SYSTEM USING COMPATIBLE EXTERNAL DEVICE

CROSS REFERENCE TO RELATED APPLICATION

This Application is a Section 371 National Stage Application of International Application No. PCT/KR2022/006266, filed May 2, 2022, the contents of which is hereby incorporated by reference in its entirety.

TECHNICAL FIELD

The present disclosure relates to a cochlear implant system.

BACKGROUND ART

Unless stated otherwise in this specification, the contents described in this section are not the related art about the claims of this application and not all of the contents described in this section are regarded as the related art.

A cochlear implant is a device that is implanted in a cochlear duct, converts external sound into a stimulation signal, and stimulates the cochlea duct through the stimulation signal when the hearing ability of a patient with hearing loss due to a cochlear disease does not get better through a hearing aid.

In general, cochlear implants are composed of an external device that is worn outside and an internal device that is implanted in a body. The external device converts sound generated outside into an electrical signal and the internal device converts the electrical signal converted by the external device into an electrical stimulation signal, thereby stimulating a cochlear duct.

The internal device is supposed to generate an electrical stimulation signal in accordance with the conditions of the body or the hearing ability of a user. Accordingly, the external device is set on the basis the characteristics of a user for the internal device.

For this reason, there is a problem that when a left external device is used as a right external device or another person uses an external device, the external device is not compatible with the corresponding internal device, so the internal device cannot generate an appropriate electrical stimulation signal.

Further, there is a problem that an excessive electrical stimulation signal may be generated and may cause hearing loss or pain due to wrong use of the external device that is not compatible with the internal device.

DISCLOSURE

Technical Problem

An objective of the present disclosure is to provide a cochlear implant system in which an external device is compatible with other internal devices by keeping mapping data, which are obtained by measuring a biological response to an electrical stimulation signal of an internal device implanted in a cochlea of a user, for each internal device.

Another objective of the present disclosure is to provide a cochlear implant system in which an external device can determine there is compatibility by checking an ID assigned to an internal device.

Another objective of the present disclosure is to provide a cochlear implant system in which an external device transmits a KEY assigned to an internal device to the internal device, whereby the internal device can check whether the external device is a reliable external device.

Technical Solution

A cochlear implant system using a compatible external device includes: an external device keeps mapping data, which are obtained by measuring a biological response to an electrical stimulation signal of an internal device implanted in a cochlear conduct of a user, for each internal device, determines whether there is compatibility with a target internal device, and converts sound into an electrical signal in accordance with mapping data of the target internal device of a plurality of pieces of mapping data; and a target internal device receives an electrical signal from the external device, converts the electrical signal into an electrical stimulation signal, and stimulates the auditory nerve of a cochlea with the electrical stimulation signal when the external device is compatible.

Advantageous Effects

Since the external device keeps mapping data, which are obtained by measuring a biological response to an electrical stimulation signal of an internal device implanted in a cochlear conduct of a user, for each internal device, it is possible to use mapping data of a corresponding internal device when converting sound into an electrical signal, so it is possible to synchronize an internal device using an external device of another person and it is also possible to use the external device regardless of the left and right, whereby the present disclosure has an effect that convenience for a user can be maximized.

Further, since the external device can determine whether there is compatibility by checking the ID assigned to an internal device, the external device does not generate an electrical signal for an incompatible internal device, so the present disclosure has an effect that it is possible to prevent hearing loss or pain due to a wrong electrical signal.

Further, since the external device transmits the KEY assigned to an internal device and the internal device can check whether the external device is a reliable external device, the present disclosure has an effect that it is possible to improve security by preventing hacking by other people.

MODE FOR INVENTION

Figure 1:
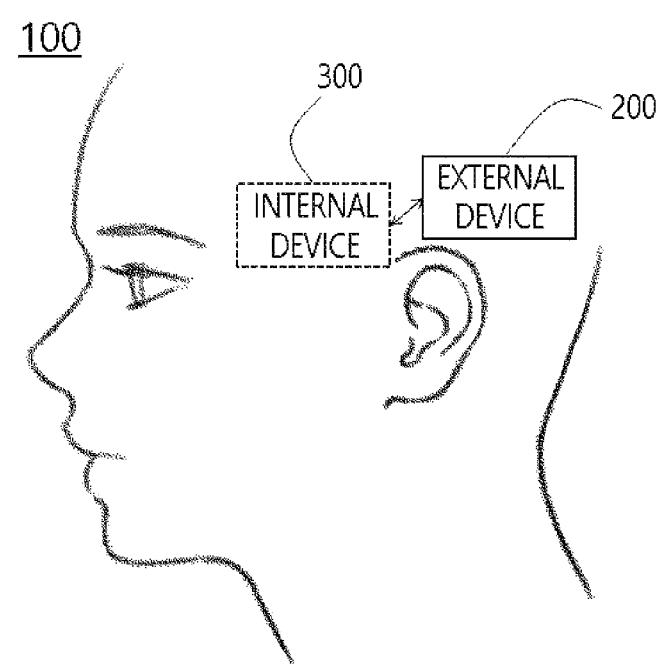
FIG. 1 is a view showing a cochlear implant system using a compatible external device according to an embodiment of the present disclosure.

It should be noticed that when reference numerals are given to components in the drawings in the specification, the same components are given the same numbers even if they are not shown in different drawings.

Meanwhile, the meanings of the terms used herein should be understood as follows. Singular forms should be understood as including plural forms unless the context clearly indicates otherwise, terms "first", "second", etc. are used to distinguish one component from another component, and the range of the right should not be limited by the terms. It should be understood that terms "comprise" or "have" do not exclude the possibility of existence or addition of one or more other features, numbers, steps, operations, components, parts, or a combination thereof.

It should be understood that the term "at least one" includes all combinations that can be proposed from one or more associated items. For example, the meaning of "at least one of a first item, a second item, and a third item" means not only each of the first item, the second item, or the third item, but also all combinations that can be presented from two or more of the first item, the second item, and the third item.

Hereinafter, embodiments of the present disclosure are described with reference to the accompanying drawings.

FIG. 1 is a view showing a cochlear implant system using a compatible external device (hereafter, referred to as "cochlear implant system") according to an embodiment of the present disclosure.

A cochlear implant system 100 enables a patient having damage to the cochlea to recover his/her hearing by directly providing electrical stimulation to the auditory nerve. To this end, the cochlear implant system 100 according to the present disclosure converts sound generated outside into an electrical signal and converts the electrical signal into an electrical stimulation signal that can stimulate a cochlear duct. The cochlear implant system 100 stimulates a cochlea duct with a converted electrical stimulation signal. The cochlear implant system 100 can stimulate the auditory nerve included in a cochlear duct.

The cochlear implant system 100, as shown in FIG. 1, includes an external device 200 and a target internal device 300.

The external device 200 according to the present disclosure can be compatible to a plurality of different internal devices. In the related art, when a user implanted with cochlear implants in both ears, the internal device 300 implanted in the left ear is not compatible with the external device 200 worn on the right ear, and vice versa. Further, when all family members are implanted with cochlear implants and their external devices 200 are switched, the external devices 200 are not compatible with their internal devices 200.

Further, when a user wears an external device 200 that is not compatible with the internal device 300 implanted in the user, there is a problem that a wrong signal is input to the internal device 300 from the external device 200 and pain is caused or the auditory nerve is damaged due to electrical stimulation that is not compatible with the user.

However, there is an effect that since the external device 200 according to the present disclosure can be compatible with internal devices 300 implanted in users, so the external device 200 can be used for both ears regardless of the direction and can be used among family members. Further, there is an effect that the external device 200 according to the present disclosure can prevent pain and damage to the auditory nerve due to an incompatible external device 200.

The external device 200 according to the present disclosure keeps mapping data obtained by measuring a biological response to an electrical stimulation signal of an internal device 300. The external device 200 may keep a plurality of pieces of data measured for a plurality of internal devices 300, respectively. The mapping data means data obtained by measuring the auditory response characteristics of an ear to operate an internal device 300 appropriately to the body of a user after the internal device 300 is implanted in the body of the user.

In an embodiment, the mapping data may include a biological response of a user to the magnitude of an electrical stimulation signal, a biological response of a user to the frequency of an electrical stimulation signal, a biological response of a user to the pattern of an electrical stimulation signal, etc.

The reason that the external device 200 according to the present disclosure keeps a plurality of pieces of mapping data is because states such as the degree of damage or the degree of sensitivity of the auditory nerves in the *cochleae* of users are different, so electrical simulation signals should be differently input from internal devices 300. Accordingly, the external device 200 according to the present disclosure keeps mapping data of each of internal devices 300 and can be compatible with the internal devices 300 using the mapping data corresponding to target internal devices 300.

The external device 200 according to the present disclosure converts sound into an electrical signal. In detail, the external device 200 converts sound generated outside into an electrical signal and transmits the electrical signal to an internal device 300. Accordingly, the internal device 300 can stimulate the auditory nerve of a cochlea in response to the electrical signal from the external device 200.

In an embodiment, the external device 200 can determine whether there is compatibility with a target internal device 300. The external device 200 can convert sound into an electrical signal in accordance with the mapping data of the target internal device 300 of a plurality of pieces of mapping data, depending on whether there is compatibility.

In an embodiment, the external device 200 keeps ID values assigned to a plurality of internal devices, respectively. According to this embodiment, the external device 200 may map and keep mapping data and IDs.

In an embodiment, the external device 200 can determine whether there is compatibility by determining whether the ID assigned to a target internal device 300 exists in a plurality of IDs. The external device 200 can determine that there is compatibility with the target internal device 300 when the ID assigned to the target internal device 300 exists in the plurality of IDs. The external device 200 can determine that there is no compatibility with the target internal device 300 when the ID assigned to the target internal device 300 does not exist in the plurality of IDs.

In an embodiment, when determining that there is compatibility with the target internal device 300, the external device 200 can extract mapping data mapped with the corresponding ID from a plurality of pieces of mapping data. The external device 200 can convert sound into an electrical signal by applying the extracted mapping data.

In an embodiment, when determining that there is no compatibility with the target internal device 300, the external device 200 does not transmit an electrical signal to the target internal device 300.

In an embodiment, the external device 200 keeps IDs and KEYs assigned to a plurality of internal devices, respectively. According to this embodiment, the external device 200 may map and keep mapping data and the IDs and KEYS.

The reason that the external device 200 according to the present disclosure keeps the respectively KEYs of a plurality of internal devices is for improving security performance through the KEYs assigned to the internal devices, respectively, because internal devices are directly implanted in a body and the body itself may be damaged due to hacking or authentication by other people.

In an embodiment, the external device 200 can determine whether there is compatibility by determining whether the ID and the KEY assigned to a target internal device 300 exist in a plurality of IDs and KEYs. The external device 200 can determine that there is compatibility with the target internal device 300 when the ID and the KEY assigned to the target internal device 300 exist in the plurality of IDs and KEYs. The external device 200 can determine that there is no compatibility with the target internal device 300 when at least one of the ID and the KEY assigned to the target internal device 300 does not exist in the plurality of IDs.

In an embodiment, when the ID assigned to a target internal device 300 exists in a plurality of IDs, the external device 200 can transmit a KEY mapped to the ID to the target internal device 300. According to this embodiment, the target internal device 300 can determine whether the received KEY is the same as the assigned KEY, and can transmit the result of checking the KEYs to the external device 200. When determining that the KEYs are the same as the result of checking the KEYs received from the target internal device 300, the external device 200 can determine that there is compatibility with the target internal device 300.

As described above, the external device 200 primarily determines whether there is compatibility on the basis of an ID received through a target internal device 300 and the target internal device 300 secondarily determines whether a KEY received from the external device 200 is the same as an assigned KEY, whereby the present disclosure has an effect that it is possible to prevent the external device 200 from one-sidedly connecting with an internal device and thus security performance is improved.

In an embodiment, when determining that there is compatibility with the target internal device 300, the external device 200 can extract mapping data mapped to the corresponding ID and KEY from a plurality of pieces of mapping data. The external device 200 can convert sound into an electrical signal by applying the extracted mapping data.

In an embodiment, when determining that there is no compatibility with the target internal device 300, the external device 200 does not transmit an electrical signal to the target internal device 300.

Figure 2:
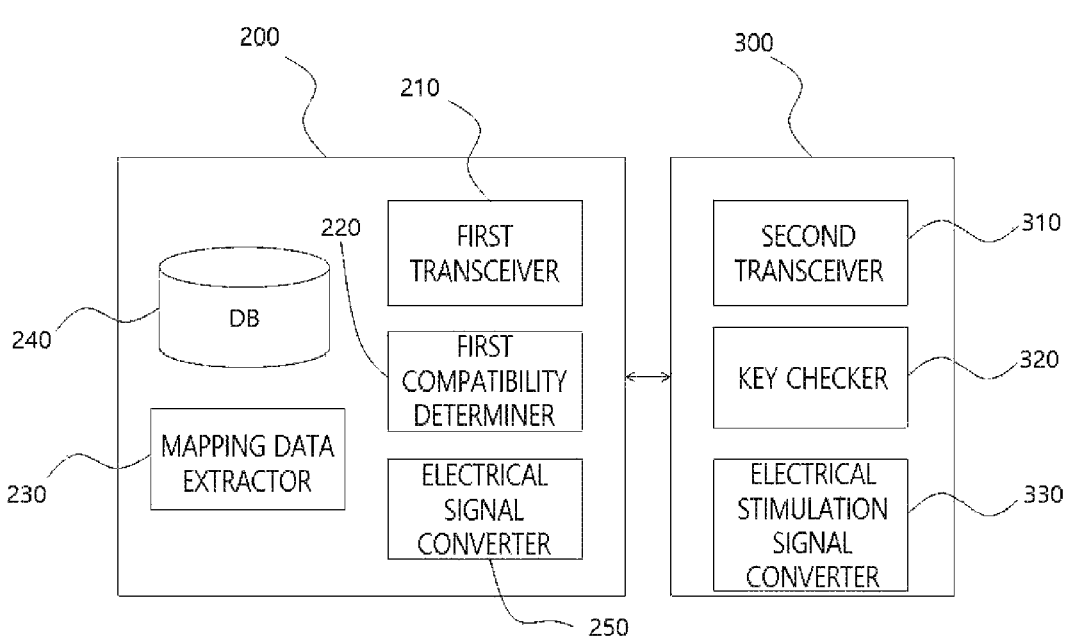
FIG. 2 is a view showing an example of the configuration of an external device and an internal device of the present disclosure.

Hereafter, the external device 200 according to the present disclosure is described in more detail with reference to FIG. 2. FIG. 2 is a view showing an example of the configuration of an external device and an internal device of the present disclosure. The external device 200 according to the present disclosure, as shown in FIG. 2, includes a first transceiver 210, a first compatibility determiner 220, a mapping data extractor 230, a database 240, and an electrical signal converter 250.

The first transceiver 210 performs transmission/reception with a target internal device 300. The first transceiver 210 can receive the ID assigned to the target internal device 300 from the target internal device 300. Further, the first transceiver 210 can transmit the KEY mapped to the ID to the target internal device 210. Further, the first transceiver 210 can transmit whether there is compatibility to the target internal device 300.

The first compatibility determiner 220 determines whether there is compatibility by comparing the ID received from the target internal device 300 with a plurality of IDs kept in the database 240. In detail, the first compatibility determiner 220 determines that there is compatibility when the ID received from the target internal device 300 exists in the plurality of IDs kept in the database 240. The first compatibility determiner 220 determines that there is no compatibility when the ID received from the target internal device 330 does not exist in the plurality of IDs kept in the database 240.

In an embodiment, when the ID received from the target internal device 330 exists, the first compatibility determiner 220 can transmit the KEY mapped to the ID to the target internal device 300 through the first transceiver 210.

According to this embodiment, the target internal device 300 determines whether its KEY is the same as the transmitted KEY, and transmits the result of checking the KEYs to the first compatibility determiner 220 through the first transceiver 210.

The first compatibility determiner 220 can determine that there is compatibility when, as the result of checking the KEYs, the KEYs are the same. The first compatibility determiner 220 can determine that there is no compatibility when, as the result of checking the KEYs, the KEYs are not the same.

The first compatibility determiner 220 can transmit whether there is compatibility to the target internal device 300 through the first transceiver 210.

In an embodiment, when it is determined that there is compatibility by the first compatibility determiner 220, the mapping data extractor 230 can extract the mapping data, which are mapped and kept for the ID assigned to the target internal device 300, from the plurality of mapping data kept in the database 240. The mapping data extractor 230 transmits the mapping data to the electrical signal converter 250.

A plurality of IDs, a plurality of KEYS, and a plurality of pieces of mapping data are kept in the database 240. The plurality of pieces of mapping data may be mapped and kept for the plurality of IDs, respectively. The plurality of pieces of mapping data may be mapped and kept for the plurality of IDs, respectively, and the plurality of KEYs, respectively.

The electrical signal converter 250 converts sound in to an electrical signal. In detail, the electrical signal converter 250 can convert sound into an electrical signal in accordance with the mapping data extracted by the mapping data extractor 230. Accordingly, the electrical signal converter 250 can generate an electrical signal to fit to the target internal device 300.

In an embodiment, when it is determined that there is compatibility by the first compatibility determiner 220, the electrical signal converter 250 converts sound into an electrical signal. When it is determined that there is no compatibility by the first compatibility determiner 220, the electrical signal converter 250 does not convert sound into an electrical signal.

Meanwhile, referring to FIG. 1 again, the target internal device 300 converts an electrical signal of the external device 200 into an electrical stimulation signal and stimulates the auditory nerve of a cochlea with the electrical stimulation signal. Accordingly, a user implanted with the target internal device 300 can recognize sound through the internal device 300 even though the user has damage to a cochlea.

In an embodiment, a target internal device 300 determines whether the external device 200 is compatible. In an embodiment, a target internal device 300 transmits the ID assigned to the target internal device 300 to the external device 200, and determines that the external device 200 is compatible when the external device 200 has the ID assigned to the target internal device 300. The target internal device 300 determines that the external device 200 is not compatible when the external device 200 does not have the ID assigned to the target internal device 300.

In an embodiment, when the external device 200 has the ID assigned to the target internal device 300, the target internal device 300 can receive a KEY from the external device 200 and determine whether the KEY is the same as the KEY assigned to the target internal device 300. According to this embodiment, the target internal device 300 can determine whether the KEY transmitted from the external device 200 and its KEY are the same. The target internal device 300 transmits the result of checking the KEYs to the external device 200. The result of checking KEYs may include information showing that the KEY of the target internal device 300 and the KEY transmitted from the external device are the same when the KEYs are the same and information showing that the KEY of the target internal device 300 and the KEY transmitted from the external device are not the same when the KEYs are not the same.

As described above, since the target internal device 300 examines the KEY that the external device 200 has, the present disclosure has an effect that security performance can be improved.

In an embodiment, when it is determined that the external device 200 is compatible, the target internal device 300 can receive an electrical signal from the external device 200.

In an embodiment, when it is determined that the external device 200 is compatible, the target internal device 300 can convert the electrical signal received from the external device 200 into an electrical stimulation signal. The target internal device 300 can output the electrical stimulation signal to the auditory nerve of a cochlea.

In an embodiment, when it is determined that the external device 200 is not compatible, the target internal device 300 may not convert the electrical signal received from the external device 200 into an electrical stimulation signal. According to this embodiment, when it is determined that there is no compatibility, the target internal device 300 may not receive an electrical signal from the external device 200, may receive an electrical signal but not convert the electrical signal into an electrical stimulation signal, and may convert the electrical signal into an electrical stimulation signal but not output the electrical stimulation signal to the auditory nerve of a cochlea.

Hereafter, the target internal device 300 is described in more detail with reference to FIG. 2.

As shown in FIG. 1, the target internal device 300 includes a second transceiver 310, a KEY checker 320, and an electrical stimulation signal converter 330.

The second transceiver 310 performs transmission/reception with the external device 200. The second transceiver 310 transmits the ID assigned to the target internal device 300 to the external device 200. The second transceiver transmits the result of checking KEYs to the target internal device 300. Further, the second transceiver 310 receives a KEY from the external device 200. The second transceiver 310 receives whether there is compatibility from the external device 200.

The KEY checker 320 determines whether the KEY received from the external device 200 is the same as the KEY of the target internal device 300 when the external device 200 has the ID assigned to the target internal device 300. The KEY checker 320 transmits the result of checking the KEYs to the external device 200 through the second transceiver 310. The result of checking KEYs is information showing whether a received KEY and an assigned KEY are the same.

When it is determined that there is compatibility with the external device 200, the electrical stimulation signal converter 330 converts the electrical signal received from the external device 200 into an electrical stimulation signal, thereby stimulating the auditory nerve of a cochlea. The electrical stimulation signal converter 330 does not convert the electrical signal into an electrical stimulation signal when it is determined that there is no compatibility with the external device 200.

An example of the method of determining whether the external device 200 and the target internal device 300 are compatible in the embodiment described above is described with reference to FIGS. 3 and 4.

Figure 3:
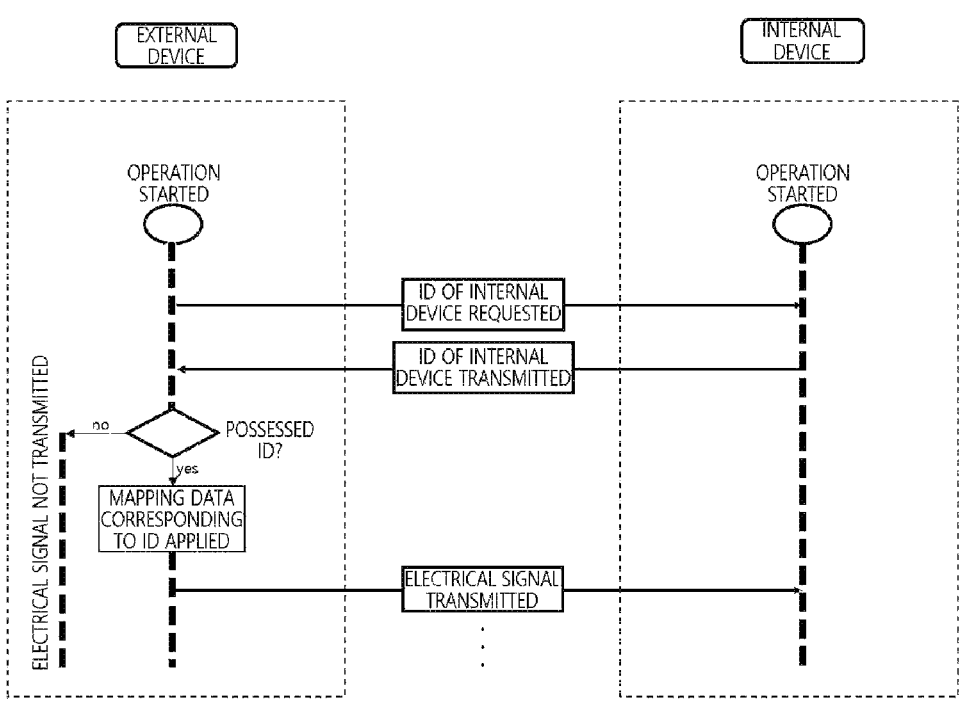
FIG. 3 is a flowchart showing the operation of determining whether there is compatibility using an ID assigned to a target internal device according to an embodiment of the present disclosure.

FIG. 3 is a flowchart showing the operation of determining whether there is compatibility using the ID assigned to a target internal device 300 according to an embodiment of the present disclosure.

As shown in FIG. 3, the external device 200 requests the assigned ID from an internal device 300. The internal device 300 transmits the assigned ID and the external device 200 determines whether the transmitted ID exists in a plurality of IDs kept in advance. The external device 200 does not convert sound into an electrical signal when the transmitted ID does not exist in the plurality of IDs. When the transmitted ID exists in the plurality of IDs, the external device 200 extracts the mapping data mapped to the transmitted ID from a plurality of pieces of mapping data kept in advance. The external device 200 converts sound into an electrical signal by applying the extracted mapping data. The external device 200 transmits the converted electrical signal to the internal device 300. The internal device 300 converts the transmitted electrical signal into an electrical stimulation signal, thereby stimulating the auditory nerve of a cochlea.

Figure 4:
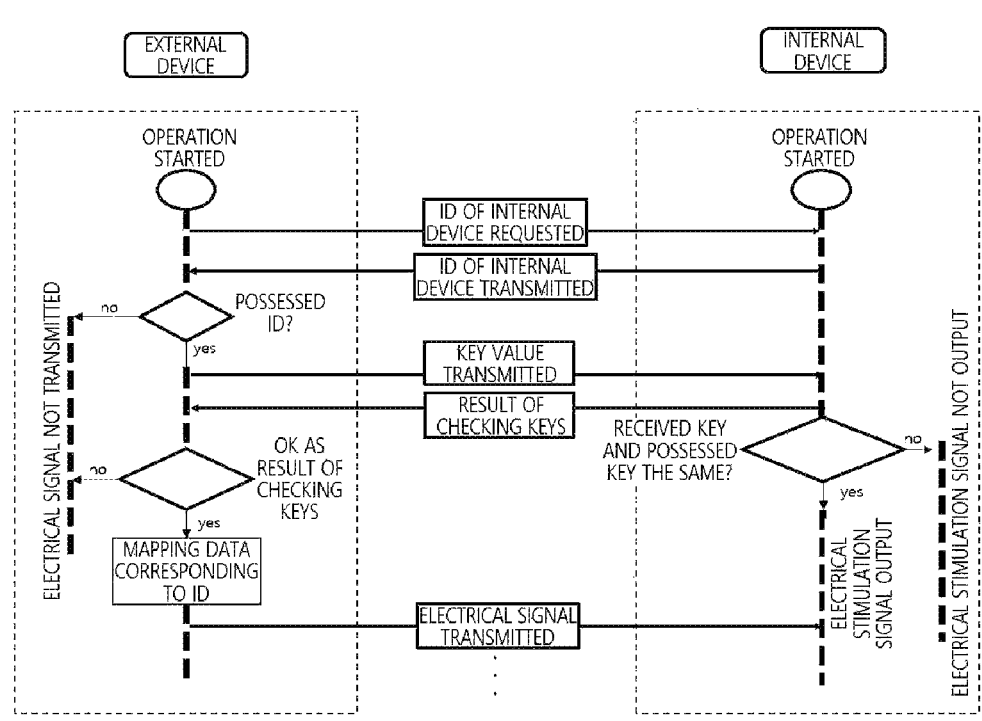
FIG. 4 is a flowchart showing the operation of determining whether there is compatibility using an ID and a KEY assigned to a target internal device 300 according to an embodiment of the present disclosure.

FIG. 4 is a flowchart showing the operation of determining whether there is compatibility using an ID and a KEY assigned to a target internal device 300 according to an embodiment of the present disclosure. As described above, the present disclosure can improve security by assigning not only an ID, but also a KEY to a target internal device 300.

As shown in FIG. 3, the external device 200 requests the assigned ID from a target internal device 300. The target internal device 300 transmits the assigned ID and the external device 200 determines whether the transmitted ID exists in a plurality of IDs kept in advance. The external device 200 does not convert sound into an electrical signal when the transmitted ID does not exist in the plurality of IDs. When the transmitted ID exists in the plurality of IDs, the external device 200 transmits the KEY mapped to the ID in the plurality of IDs kept in advance to the target internal device 300. The target internal device 300 determines whether the received KEY is the same as the assigned KEY, and transmits the result of checking the KEYs to the external device 200.

The external device 200 does not convert sound into an electrical signal when the target internal device 300 determines that the received KEY does not coincide with the assigned KEY.

The external device 200 converts sound into an electrical signal by applying the mapping data mapped to the assigned ID in a plurality of pieces of mapping data when the target internal device 300 determines that the received KEY coincides with the assigned KEY.

The external device 200 transmits the converted electrical signal to the target internal device 300.

When the received KEY coincides with the assigned KEY, the target internal device 300 converts the received electrical signal into an electrical stimulation signal, thereby stimulating the auditory nerve of a cochlea.

The target internal device 300 does not output an electrical stimulation signal when the received KEY does not coincide with the assigned KEY.

Those skilled in the art could understand that the present disclosure can be achieved in other detailed ways without changing the spirit or the necessary features of the present disclosure. When the present disclosure is achieved by a plurality of separate programs, the programs may be recorded on different media, respectively.

Therefore, the embodiments described above are only examples and should not be construed as being limitative in all respects. The scope of the present disclosure is defined by the following claims rather than the above detailed description, and all of changes and modifications obtained from the meaning and range of claims and equivalent concepts should be construed as being included in the scope of the present disclosure.

The invention claimed is:

1. A cochlear implant system using a compatible external device that includes an external device and a target internal device, wherein the external device keeps mapping data, which are obtained by measuring a biological response to an electrical stimulation signal of the target internal device implanted in a cochlear conduct of a user, for each target internal device, determines whether there is compatibility with a target internal device, and converts sound into an electrical signal in accordance with mapping data of the target internal device of a plurality of pieces of mapping data; and the target internal device receives an electrical signal from the external device, converts the electrical signal into an electrical stimulation signal, and stimulates the auditory nerve of a cochlea with the electrical stimulation signal when the external device is compatible, wherein the external device maps ID values assigned to a plurality of internal devices, respectively, to the mapping data and keeps the ID values, and when an ID that coincides with an ID value of the target internal device exists in a plurality of IDs, the external device extracts mapping data mapped to the ID and converts the sound into an electrical signal in accordance with the extracted mapping data, wherein the external device keeps KEYs assigned to a plurality of internal devices, respectively, and does not convert sound into the electrical signal when a KEY that coincides with a KEY of the target internal device does not exist in a plurality of KEYS, wherein when at least one of an ID and a KEY assigned to the target internal device of a plurality of IDs and KEYs does not coincide with an ID or KEY stored in the external device, the external device determines that the target internal device is not compatible, and does not transmit an electrical signal to the target internal device, wherein the external device maps IDs and KEYs assigned to a plurality of internal devices with the mapping data and keeps the IDs and the KEYs, and when an ID stored in the external device coinciding with an ID transmitted from the target internal device, the external device transmits the KEY of the ID to the internal device, wherein the target internal device determines that the external device is compatible when the KEY of the ID coincides with an assigned KEY, and wherein when a KEY received from the external device does not coincide with an assigned KEY, the target internal device determines that the external device is not compatible, and does not stimulate the auditory nerve of the cochlea in response to an electrical signal received from the external device.

2. The cochlear implant system of claim 1, wherein the mapping data includes at least one of a biological response of a user to a magnitude of an electrical stimulation signal, a biological response of a user to a frequency of an electrical stimulation signal, a biological response of a user to a pattern of an electrical stimulation signal.

* * * * *